United States Patent [19]

Nelson et al.

[11] Patent Number: 4,701,443

[45] Date of Patent: Oct. 20, 1987

[54] NUTRIENT POLYESTERS

[75] Inventors: Deanna Nelson, Morton Grove; Bruce Rowe, Chicago, both of Ill.

[73] Assignee: Baxter Travenol Laboratories, Inc., Deerfield, Ill.

[21] Appl. No.: 477,792

[22] Filed: Mar. 22, 1983

[51] Int. Cl.$^4$ ..................... A61K 31/70; C07H 13/00
[52] U.S. Cl. ..................................... 514/23; 536/1.1; 536/115
[58] Field of Search ...................... 424/311, 313, 180; 514/23; 536/115, 1.1

[56] References Cited

U.S. PATENT DOCUMENTS

| | | |
|---|---|---|
| 2,258,168 | 10/1941 | White . |
| 2,305,621 | 12/1942 | Kremers . |
| 2,407,001 | 9/1946 | Griffin . |
| 2,929,764 | 3/1960 | Hultin et al. . |
| 2,931,797 | 4/1960 | Gibbons et al. . |
| 3,640,847 | 2/1972 | Armbruster et al. ................ 435/97 |
| 3,654,082 | 4/1972 | Abdullah ............................. 435/98 |
| 3,729,461 | 4/1978 | Pomeranz et al. . |
| 3,773,946 | 11/1973 | Creger ................................ 424/313 |
| 3,963,699 | 6/1976 | Ruzzi et al. ......................... 424/180 |
| 4,005,196 | 1/1977 | Jandaceh et al. ................... 424/180 |
| 4,011,389 | 3/1977 | Langdon . |
| 4,024,278 | 5/1977 | Henrich .............................. 424/313 |
| 4,039,383 | 8/1977 | Pankratz ............................. 435/99 |
| 4,153,726 | 5/1979 | Borggrefe et al. ................. 424/180 |
| 4,172,149 | 10/1979 | Pinto et al. ........................ 424/313 |
| 4,376,789 | 3/1983 | Lowichi et al. ................... 424/180 |

OTHER PUBLICATIONS

Chemical Abstract, vol. 93, 1980, p. 494, #220384p.
Birkhahn et al., -Alternate or Supplemental Energy Soruces-Journal of Parenteral and Enteral Nutrition-vol. 5, No. 1 (1981, pp. 24-31).
Birkhahn, et al.-Intravenous Feeding of the Rat with Short Chain Fatty Acid Esters-The American Journal of Clinical Nutrition, 30-Dec. 1977-pp. 2078-2082.
Birkhahn, et a.-Intravenous Feeding of the Rat with Short Chain Fatty Acid Esters II. Monoacetoacetin-The American Journal of Clinical Nutrition, 31-Mar. 1978, pp. 436-441.
Birkhahn, et al., Monoglyceryl Acetoacetate: A Ketone Body-Carbohydrate Substrate for Parenteral Feeding of the Rat-Journal of Nutrition, 109: 1168-1174 (1979).
Birkhahn, et al.-New Synthetic Substrates for Parenteral Feeding-Journal of Parenteral and Enternal Nutrition-vol. 3, No. 5, pp. 346-349.

*Primary Examiner*—J. R. Brown
*Assistant Examiner*—Elli Peselev
*Attorney, Agent, or Firm*—Paul C. Flattery; Susan B. Fentress; Robert E. Hartenberger

[57] ABSTRACT

Synthetic polyesters are employed as calorie sources for parenteral or enteral nutrition. The polyesters are hydrolyzed and respired by the body and offer the advantage of high calorie density when compared to conventional or other synthetic calorie sources.

52 Claims, No Drawings

NUTRIENT POLYESTERS

BACKGROUND OF THE INVENTION

This invention relates to the field of nutrition, and more particularly to parenteral nutrition via peripheral veins.

Total parenteral nutrition (TPN) is a recent advance in the maintenance of patients having an impaired gastrointestinal capacity. Such patients may have lost the use of a large portion of their intestinal tract, either permanently due to surgical intervention as may be required in cancer or Crohn's disease, or temporarily as a result of chemotherapeutic drugs or in the treatment of diverticulitis. Objectives of TPN include administering all of the patient's requirements of calories and essential nutrients directly into the circulatory system, bypassing the digestive tract entirely, or administering nutrients to the remnant digestive tract in a form that will provide as much nutrition as possible without injuring either the circulatory system or the intestines.

A major difficulty in TPN has been the sensitivity of the intestines or vasculature to contact with nutrient solutions having high osmolarity. It has been necessary to use such highly concentrated solutions because at lower concentrations the nutrient solutions supply insufficient calories before exceeding the patient's ability to deal with excess diluent. Generally, a patient must receive at least 2300 ml daily of a 20% glucose solution to reach the 2000 minimum calories required, and caloric requirements can be greater in many stressed patients.

Attempts to deal with this problem have included infusing the solution via a central venous catheter. A catheter is threaded from a peripheral vein in an arm or a leg, for example, into the vena cava. Highly concentrated nutrient solutions can be passed through the catheter into the large volume of central venous blood, where rapid dilution of the solution obviates vascular injury and reduces local hemolysis. Central venous catheters, however, among other disadvantages require a special procedure to insert. It would be safer and considerably more convenient if parenteral nutrition could be administered via a peripheral vein.

Milner (U.S. Pat. No. 3,928,135) administered a high caloric solution enterally or via peripheral veins. This solution contained a mixture of glucose polymers (polyglucose). Contrary to Milner's assertion, the maltose metabolites of polyglucose are not metabolized at a sufficiently high rate by the tissues to glucose so as to supply sufficient calories but instead are largely excreted by the kidneys. Since the caloric contributions of polyglucose are considerably lower than might be calculated based on an assumption of complete metabolism through glucose, a need still remains for a low osmolar solution containing a high level of biologically available calories. Accordingly, the objectives of this invention include:

(a) providing compounds for parenteral or enteral nutrition which are biologically available, (b) providing compounds having a biologically available caloric content in considerable excess of glucose;

(c) providing compounds which are nontoxic to the vasculature, the intestines and the cellular elements of the blood; in particular, compounds which exhibit insufficient surfactant properties to hemolyze or otherwise damage erythrocytes;

(d) providing and administering to patients the above compounds in conventional parenteral solution containers along with other nutrients such as vitamins, electrolytes, trace metals and amino acids; and (e) providing compounds which are hydrolyzed by the tissues or intestinal flora to intermediate respiratory metabolites.

These and other objects will be apparent from consideration of this specification as a whole.

SUMMARY OF THE INVENTION

The foregoing objects are achieved by administration of polyesters of biologically available, nontoxic di- or tricarboxylic acids and biologically available, nontoxic normal or branched chain aliphatic compounds containing at least two hydroxyl substituents. The nutrient compositions contemplated herein include aqueous solutions, suitable for intravenous administration, of compounds having the formula

wherein

G is hydrogen, the residue of a monosaccharide, a nontoxic, biologically available normal or branched chain aliphatic group containing at least one hydroxyl or hydroxyl and keto substituent, or the radical $(QCOO)_dY-$ where QCOO— and Y are defined below and d is 1 or 2.

QCOO— is acetyl, acetoacetyl, butyryl or the residue of a nontoxic, biologically available normal or branched chain hydroxy or keto substituted aliphatic carboxylic acid having more than 4 carbon atoms;

Y is the residue of a monosaccharide, a nontoxic, biologically available normal or branched chain aliphatic group containing at least two hydroxyl substituents;

n is from 1 to about 15; provided that when n>1, —OOCACOOY— may be the same or different;

E is hydroxyl, —CACOOH, or —(OOCQ)$_d$;

A is —(CH$_2$)$_a$—C(R)(Z)(CH$_2$)$_b$C(R')(R'')—, wherein

R is hydrogen or hydroxyl;

Z is carboxyl, —OOCACOOH, —OOCQ, hydrogen or hydroxyl; provided that where R is hydroxyl, Z is not hydroxyl, and that R and Z may be taken together to be oxy;

a is zero or an integer from 1 to about 5;

b is zero or an integer from 1 to about 5; provided that the sum of a and b is an even number, one, or zero; and R' and R'' are both hydrogen, hydrogen and hydroxy or, taken together, oxy;

and physiologically acceptable salts thereof.

The foregoing objects are also achieved by enteral or parenteral administration of novel compounds having the formula

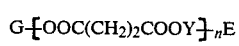

wherein G is (QC with QCOO— being a radical of the formula

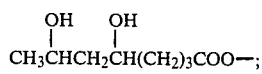

-continued

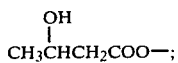

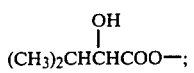

Y is —CH$_2$CH(OH)CH$_2$— or —CH$_2$CH$_2$CH(CH$_3$)—;
n is 1 to 3;
E is hydroxyl or —OOCQ as defined above; and
d is 1 or 2.

DETAILED DESCRIPTION OF THE INVENTION

The fundamental reasoning underlying this invention is that by linking biologically available polyhydroxyl and polycarboxylic acids by ester bonds, a high calorie compound is obtained that is readily hydrolyzed in the body to low molecular weight intermediary metabolites, or to low molecular weight substances which are readily converted to such intermediates.

"Biologically available" as that term is used herein means that the polyester and its ester hydrolysis products are substantially oxidized in the body to CO$_2$, H$_2$O or other low molecular weight products excreted as ordinary byproducts of tissue respiration.

Certain normal or branched chain aliphatic groups containing one or more hydroxyl or keto substituents, as well as certain normal or branched chain hydroxy or keto substituted aliphatic mono-, di- or tricarboxylic acids, are widely recognized as toxic, e.g. methanol and ethylene glycol, and oxalic, glutaric, mucic, and tartaric acids. These substances will be apparent to those skilled in the art, and are not to be employed as components in assembling the polyesters herein. "Nontoxic" polyesters or hydrolysis products are those which exhibit an LD$_{50}$ in mice at greater than 1 g/Kg body weight upon continuous administration by the route contemplated for the polyester, e.g. oral or parenteral.

The compositions of this invention include polyester compounds having the formula G—[OOCACOOY]$_n$E.

The radical —OOCOO— is the residue of the di- or tricarboxylic acid esterified to the polyhydroxy G and Y components. The structure of radical A is not critical except insofar as the di- or tricarboxylic acid of which it is a part is nontoxic and biologically available. The group "A" ordinarily will have the structure —(CH$_2$)$_a$—C(R)(Z)(CH$_2$)$_b$C(R')(R")—, wherein preferably R is hydrogen, Z is hydrogen, hydroxyl, or —OOCQ. The designation "a" is zero or 1, b is zero or 1, the sum of a and b is zero or one, and R' and R" are both hydrogen or, taken together, oxy. The group "A" is preferably the residue of a Krebs cycle carboxylic acid, especially a dicarboxylate such as succinate, alpha-ketoglutarate, malate or oxaloacetate. Succinate is most preferred. The tricarboxylate intermediates such as citrate, isocitrate and cis-aconitate are not preferred.

G is a polyhydroxy residue falling into several classes. First are the monosaccharides, including the pentoses or hexoses and their corresponding ketoses. Suitable monosaccharides may be reducing sugars such as glucose or fructose or nonreducing sugars such a sorbose or mannose. The corresponding sugar alcohols such as sorbitol or mannitol also may be employed, although these are not preferred because their rate of biological utilization is not as high as monosaccharides. The monosaccharide or sugar alcohol is esterified to the carboxylate groups through any of the hydroxyl groups of the monosaccharide or sugar alcohol, but generally the 1 or 6, or 1 or 5 positions are preferred. The same positions may be esterified at each occurrence of the monosaccharide or sugar alcohol, or different positions can be selected at each occurrence.

G is ideally not hydrogen, as the resulting carboxylates require provision for neutralizing cations. Metal ion cations such as the alkali metals must be excreted to maintain electrolyte balance, and this can place an unwarranted burden on patients with renal insufficiency.

The preferred embodiments generally contemplate at least a carboxylate diester of the terminal polyhydroxy residues, resulting in G having the structure (QCOO)$_d$—Y—. The number of terminal esters, d, is preferably one although disubstitution is possible with otherwise highly water soluble polyesters. QCOO— is acetyl, butyryl, acetoacetyl or the residue of a nontoxic biologically available normal or branched chain hydroxy- or keto- substituted aliphatic carboxylic acid having more than 4 carbon atoms. The carboxylic acid generally will have from 4 to 10 carbon atoms, ordinarily 4 to 6, and is preferably normal. The number of hydrophilic substituents should be directly proportional to the number of carbon atoms, with a greater proportion in the case of a branched chain carbon skeleton. QCOO— groups include alpha keto acids, hydroxylated fatty acids and ketone bodies, the latter most being preferred. Representative QCOO— is groups include

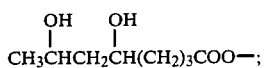

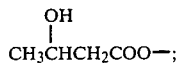

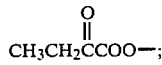

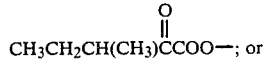

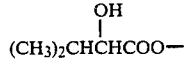

Preferably, QCOO— is the residue of a ketone body, e.g. acetoacetyl or 3-hydroxybutyryl.

Group G also may be the residue of a nontoxic, biologically available normal or branched chain aliphatic group containing at least one hydroxyl substituent, whether or not additionally oxy substituted. Preferably, however, the aliphatic groups do not contain a keto substituent. The aliphatic group also should be normal as this enhances the water solubility of the polyester. Synthesis of the polyester is simplified if G and the total of Y plus E are the same, i.e., if G is the residue of at least a dihydroxy compound. Exemplary aliphatic groups are $(CH_2OH)_2CH-$, $CH_2(OH)CH(OH)CH_2-$ and $CH_3CH(OH)CH_2CH_2-$, with the 1- or 3-glyceryl ester being most preferred.

The hydroxyl terminal end of the polyester may remain as such, whereupon E is hydroxyl, or one or two of the Y hydroxyl groups may be further esterified with one or two of the groups QCOO— described above. Alternatively, and less preferably, the terminal hydroxyl can be further esterified with a di- or tricarboxylic acid, yielding the group —OOCACOOH wherein A is as defined above. Preferably E is a QCOO— monoester (where d therefore is 1). Preferred and exemplary QCOO— groups are discussed above in connection with the G radical.

The general molecular weight of the nutrient polyesters is determined by the number of polyester groups, in turn a function of n. Higher levels of n, e.g. 10 to 15, ordinarily are not preferred, because while such polymers contain an extremely high mole calorie content, they are also more slowly utilized by the body and are less soluble than the lower molecular weight polymers. Thus, n can be higher if G is selected from monosaccharides, sugar alcohols or aliphatic groups having one or more free ketone or hydroxyl substituents after esterification, and E is hydroxyl. Also, polymers with high n value can be solubilized by small amounts of cosolvents such as ethanol or glycerol although this is not preferred because the cosolvents frequently are biologically active in their own right and will complicate therapy. Preferably, n is only 1 or 2.

Selection of groups G, A, Y and E will have the objective of optimizing several characteristics of the resulting polyester. First, the polyester must be soluble at room temperature in substantially neutral aqueous solutions, e.g. those having a pH of about from 5.5 to 7.5. Thus, radicals having aliphatic groups greater than $C_3$ will need to be used sparingly to improve the water solubility of the polyesters. However, even poorly soluble polyesters can be employed as supplements to other nutrients or other more soluble polyesters. Generally, solubility of greater than about 3 mole percent in water at room temperature is satisfactory.

The second characteristic is biological availability, as defined briefly above. The polyesters must be hydrolyzed in the body after infusion or ingestion, although the manner in which this occurs is not as important as the fact that it does. Monoesters should be selected which are susceptible to solvolysis or hydrolysis upon contact of the polyester with components such as hydrogen ions present in the blood; Esters selected for susceptibility to solvolysis will contain —OOCQ or Y groups with polar functional groups at the 3 or 5 carbon positions.

Most likely hydrolysis is the primary result of enzymatic action in blood cells, plasma and body tissues and organs. Also, enzymatic hydrolysis by intestinal flora will occur after enteral administration.

Hydrolysis will be dependent upon many factors. Some polyesters may be optimal in the TPN of a patient with gastro-intestinal disease while the same polyesters might not be optimal for a patient with liver disease if the polyester is principally hydrolyzed by liver enzymes. Thus, the clinician must use some discretion in selecting polyesters for optimal biological availability. The experimental method for the selection will be relatively straightforward, however. The ultimate criterion is stabilization of weight loss, or a gain in weight, in the patient being treated. A more immediate assay for availability would be to determine plasma increases in representative polyester hydrolysis products, e.g. glycerol or dicarboxylic acid. In such a case a polyester is biologically available if it is hydrolyzed in the body at a rate sufficient to supply nutrition. This rate may be quite low, however, if the polyester is to serve as a supplementary nutrient. The polyester must be nontoxic as defined above. However, it may be of value to select polyesters on the basis of more specific toxicity data than lethal dose in mice. For example, esters should be selected which do not irreversibly inhibit the enzymes of the Kreb's cycle. This is readily determined by assaying the particular enzyme activity on a given, usually normal physiological, substrate for the enzyme in the presence or absence of the polyester or its hydrolysis products It should be noted that competitive, reversible inhibition of existing enzyme systems by the polyesters or their hydrolysis products is not disadvantageous. In fact, one feature of this invention is that hydrolysis of the polyesters is in part dependent upon the unexpectedly fortuitous existence of unfastidious esterases which ordinarily hydrolyze other substrates in the body. The administration of the polyesters may result in some transient inhibition of these normal hydrolytic activities, but induction of greater amounts of the enzymes in question soon will overcome any such inhibition.

Polyesters should be chosen which can be autoclaved with minimal thermal hydrolysis or other rearrangements. This will be an objective if the polyesters are to be infused parenterally, but will not be of concern where the polyesters are planned to be administered enterally. If the polyesters are thermally unstable they may be sterilized by other known methods, for example, sterile filtration.

Representative polyesters which are contemplated in the practice of this invention are described below.

TABLE I

1. $CH_2(OH)CH(OH)CH_2\text{--}[OOC(CH_2)_2COOCH_2CH(OH)CH_2]_n\text{OH}$
   n = 10
2. $CH_2(OH)CH(OH)CH_2\text{--}[OOC(CH_2)_2COOCH(CH_2OH)CH_2]_n\text{OH}$
   n = 15
3. $CH_3CH(OH)CH_2CH_2\text{--}[OOC(CH_2)_2COOCH_2CH_2CH(CH_3)]_n\text{OH}$
   n = 1
4. $CH_2(OH)CH(OH)CH_2\text{--}[OOC(CH_2)_2COOCH_2CH_2CH(CH_3)]_n\text{OOC(CH}_2)_2\text{COOCH}_2\text{CH(OH)CH}_2\text{OH}$
   n = 3
5. $CH_3CH(OH)CH_2COOCH_2CH(OH)CH_2\text{--}[OOC(CH_2)_2COOCH_2CH(OH)CH_2]_n\text{OOCCH}_2\text{CH(OH)CH}_3$
   n = 2

TABLE I-continued

6. CH₂(OH)CH(OH)CH₂₊OOC(CH₂)₂COOCH₂CH₂CH(CH₃)₎ₙOOCCH₂CH(OH)COOCH₂CH(OH)CH₂OOC—CH₂CCH₃
   ‖
   O
   n = 1

7. CH(CH₂OH)₂₊OOC(CH₂)₂COOCH(CH₂OH)CH₂₎ₙOH
   n = 5

8. CH₃CH(OH)CH₂CH₂₊OOCCH(OH)CH₂COOCH₂CH₂CH(CH₃)₎ₙOH
   n = 2

9. CH₃CH[OOCCH₂CH(OH)CH₃]CH₂CH₂₊OOC(CH₂)₂COOCH₂CH₂CH(CH₃)₎ₙOOCCH₂CH(OH)CH₃
   n = 1

10. CH₃CH(OH)CH₂CH₂₊OOC(CH₂)₂COOCH₂CH₂CH(CH₃)₎ₓ₊OOC(CH₂)₂COOCH₂CH(OH)CH₂₎ᵧOH
    x = 1; y = 2

11. CH[CH₂OOCCH₂CH(OH)CH₃]₂₊OOC(CH₂)₂COOCH₂CH₂CH(CH₃)₎ₙOOCCH₂CH(OH)CH₃
    n = 1

12. CH(CH₂OH)₂₊OOCCH₂CH(OH)COOCH₂CH(OH)CH₂₎ₙOH
    n = 12

13. CH₂[OOC(CH₂)₂COOCH₂CH(OH)CH₂]ₓ—OH
    CH(OH)
    CH₂[OOC(CH₂)₂COOCH₂CH(OH)CH₂]ᵧ—OH
    x = 1, y = 1

14.
<pre>
    ┌─CH──┐┌─OOCCH(OH)CH₂COOCH──┐
    │ HCOH ││        HCOH        │
  O │ HOCH ││        HOCH       O│
    │ HCOH ││        HCOH        │
    └─CH──┘│        ─CH─        │
      CH₂OH│        CH₂─        ├─OH
           └                    ┘ₙ
</pre>
   n = 5

15.
<pre>
    ┌─CHOH─┐   ┌─CH──┬─OH
    │ HCOH │   │ HCOH │
  O │ HOCH │ O │ HOCH │
    │ HCOH │   │ HCOH │
    └─CH──┘   └─CH──┘
      CH₂     OOC(CH₂)₂COOCH₂ ]ₙ
</pre>
   n = 1

16.
<pre>
    ┌─CHOH─┐   ┌─CH──┬─OH
    │ HCOH │   │ HCOH │
  O │ HOCH │ O │ HOCH │
    │ HCOH │   │ HCOH │
    └─CH──┘   └─CH──┘
      CH₂──OOCCH₂CH(OH)(CH₂)₂COOCH₂ ]ₙ
</pre>
   n = 2

17.
<pre>
  CH₂(OH)CH(OH)CH₂₊OOC(CH₂)₂COOCH──┐
                              HCOH │
                              HOCH │
                              HCOH O
                              CH──┘
                              CH₂──────OH ]ₙ
</pre>
   n = 1

18. CH₂(OH)CH(OH)CH₂₊OOC(CH₂)₂COOCH₂CH(OH)CH₂₎ₙOH
    n = 2

19. CH₃CH(OH)CH₂CH₂₊OOCCH(OH)CH₂COOCH₂CH(OH)CH₂₎ₙOH
    n = 1

20.
<pre>
        CH₂(OH)
       ┌─CH
       │ HOCH
     O   HCOH
       └─COH
          CH₂₊OOC(CH₂)₂COOCH₂
                 ┌─CH
                 │ HOCH
               O   HCOH
                 └─COH
                    CH₂ ]ₙ OH
</pre>

TABLE I-continued

21. 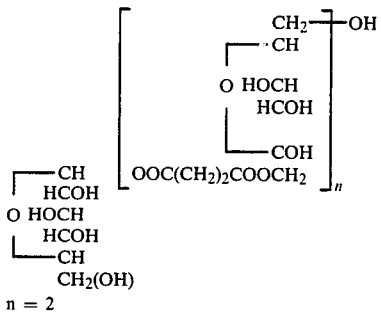
n = 2

22. 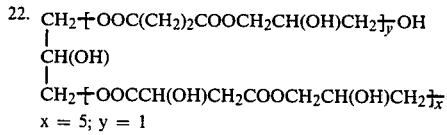
x = 5; y = 1

23. $CH_2(OH)CH(OH)CH_2\text{-}[OOC(CH_2)_2COOCH(CH_3)CH_2CH_2]_n\text{-}OOCCH_2COOH$
n = 3

24. 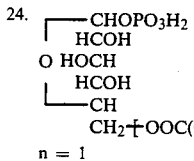
n = 1

25. $CH_3CH(OH)CH_2COOCH_2CH(OH)CH_2\text{-}[OOC(CH_2)_4COOCH_2CH(OH)CH_2]_n\text{-}OOCCH_2CH(OH)CH_3$
n = 1

26. $HOOC(CH_2)_2COO\text{-}[CH_2CH(OH)CH_2OOC(CH_2)_2COO]_n\text{-}CH_2CH(OH)CH_2OOC(CH_2)_2COOH$
n = 6

The polyesters have the principal advantage over glucose in having an extremely high available calorie density. The following Table 2 demonstrates the high energy density of the polyesters in comparison with other calorie sources.

TABLE 2

| Compound | Mole Weight | ATP* | Kcal/Mol | Parenteral Solution for TPN+ mM |
|---|---|---|---|---|
| glycerol | 92 | 19 | 228 | 2193 |
| glucose | 180 | 38 | 456 | 1096 |
| 1, 3-butanediol | 90 | 31 | 372 | 1344 |
| monobutyrin# | 162 | 48 | 576 | 856 |
| bis(diglyceryl)succinate | 266 | 65 | 780 | 640 |
| bis(3-hydroxybutyryl) succinate | 262 | 89 | 1068 | 468 |
| bis(acetoacetylglyceryl) succinate | 434 | 113 | 1356 | 370 |

Birkhahn et al. "J. Par. Ent. Nutr." 5(1):24 (1981).
*calculated adenosine triphosphate generated upon complete respiration of the compound.
+0.5 Kcal/ml solution The polyesters described herein are useful in stabilizing or increasing patient weight, reducing nitrogen loss (particularly the alpha-keto carboxylic acid esters) and effecting other metabolic and physiological improvements in the clinical state of the patient. For parenteral administration, the selected polyester or mixture of polyesters is dissolved in an aqueous solution at the desired concentration. This concentration may be that which is intended for use, e.g. about from 5 to 20 mole percent, or may be more concentrated, e.g. about from 10 up to 50 mole percent or the saturation solubility limit of the polyester. Concentrated solutions are maintained at the greater concentration to enhance the polyester stability during autoclaving or storage. Such solutions then are diluted to the desired administration concentration at some convenient point before use. If necessary, the polyester need not be dissolved in an aqueous solution at all until reconstitution before administration. This, however, is not as commercially desirable as supplying a ready-to-use solution.

The polyester solution for administration frequently will be mixed with other nutrients or with drugs. Such other nutrients may include nitrogen sources such as amino acids, essential fatty acids such as linoleic or linolenic acid, vitamins, minerals, and electrolytes including trace elements. Other calorie sources such as carbohydrates or lipids will not ordinarily be needed but may be supplied as required clinically. The amino acids are mixed with the polyester prior to or after sterilization. A mixture of essential amino acids nutritionally balanced according to the Rose proportions will ordinarily be sufficient, although nonessential amino acids may be included. The proportions may be adjusted for special disease states, e.g., inborn errors of metabolism, in accord with known practice. Supplemental nutrients also will be selected to avoid adverse effects on the polyesters during sterilization and/or storage, e.g. accelerated hydrolysis. The pH may range about from 5.5 to 7.5. Other conventional additives such as antioxidants, buffers and the like may be included as well.

The solutions are packaged in conventional parenteral solution containers, either glass or thermoplastic flexible bags. Such containers are sterile sealed and will contain means for communicating with the patient's circulation, either alone or in concert with other devices. Typically, the means for communicating with the patient's circulation will be a frangible member associated with the container which is adapted to enter into fluid communication with an administration set. Such sets also are well known.

The solutions usually are parenterally administered by infusion into a peripheral vein. The polyester concentration is not critical. It should not be so low as to introduce undue amounts of water into the patient, nor so high as to cause peripheral vascular irritation. Generally an osmolarity below about 600 mOsm. is satisfactory for peripheral parenteral infusion. Less advantageously, the solution may be infused through a central venous catheter. The solutions are infused at a rate sufficient to maintain the nutritional status of the patient in concert with the intake of other nutrients. Infusion will be ordinarily about from 25 to 40 Kcal/Kg patient weight/day, but the amount administered parenterally will depend upon the patient's oral intake of polyester or other nutrients.

The polyesters herein can be taken orally, and they have the advantage of a higher energy content than glucose so are less likely to cause diarrhea or other intestinal symptoms at a given Kcal dose when compared to glucose. The polyesters, alone or in combination with other nutrients as described above or with drugs, can be taken by gastric tube or as a component of ordinary meals.

The polyester may be made in accord with modifications of known synthetic methods. The diacid-diglyceride or the bis(diglyceride) esters of dicarboxylic acids may be synthesized by the method of Ward et al., "J. Am. Oil Chem. Soc."36:667–671 (1959) or Feuge et al., "J. Am. Chem. Soc."80:6338–6341 (1958). The bis(-monosaccharyl) derivatives may be made by the method of U.S. Pat. No. 2,893,990 using alcohol diesters as starting materials. The bis-dicarboxylate derivatives may in turn serve as the starting materials for larger polyesters. For example, a pyridine solution of diglyceryl succinate can be treated with a diacyl chloride to yield poly(diglyceryl succinate). The terminal hydroxyls may be esterified in pyridine by reaction with a diketene to yield the QCOO— groups. The tricarbox —OOCACO— compounds can be reacted as follows to form the branched polyesters:

drous $Na_2CO_3$ and filtered. The cloudy filtrate was then dried over anhydrous $MgSO_4$. The dried solution was separated by filtration to clarity and concentrated to a pale yellow oil. The yield was 27.3 g of diglyceryl succinate. Selectivity of reaction so as to obtain only diglyceryl succinates is obtained by completing the reaction in dilute solution.

Alternatively, the method of Ward et al., "J. Am. Oil Chem. Soc."36:667–671 (1959) was used except that succinyl chloride was substituted for adipyl chloride. A satisfactory yield of diglyceryl succinate was obtained.

EXAMPLE 2

Preparation of Bis(3-hydroxybutyryl)succinate

The method of Example 1 using succinic anhydride was repeated except with the substitution of 1, 3-butanediol for glycerol. Bis(3-hydroxybutyryl)succinate was recovered. Selectivity of reaction so as to obtain only bis(3-hydroxybutyryl) succinate was achieved by completing the reaction in dilute solution. Under these conditions steric interference favors esterification at carbon-1, leading to formation of the 3-hydroxy-1-butyryl esters.

EXAMPLE 3

Preparation of Bis(acetoacetylglyceryl) Succinate

Diglyceryl succinate was prepared as described in Example 1. A solution of 13.3 g of diester in anhydrous dioxane was treated with 15.6 g of 2,2,6-trimethyl-1, 3-dioxen-4-one and a catalytic amount of pyridinium p-toluenesulfonate. The reaction mixture was stirred at room temperature for 24 hours, filtered, and concentrated. The residual oil was taken up in chloroform and washed successively with a small volume of normal hydrochoric acid and with water. The organic solution was dried over anhydrous $MgSO_4$, filtered and concentrated to a yellow oil. The yield was 21.2 g of bis-(acetoacetylglyceryl) succinate.

EXAMPLE 4

Preparation of Bis(3-acetylglyceryl) Succinate

Diglyceryl succinate was prepared as described in Example 1. To a solution of 13.3 g of diester in anhydrous dioxane containing 20 ml of pyridine was added dropwise a solution of 8 g of acetyl chloride in 50 ml dioxane. During the addition the temperature was controlled by external cooling of the reaction vessel. After stirring for 12 hours, the solution was filtered and concentrated in vacuo. The residual oil was taken up in chloroform, washed successively with water, dilute acid and water, and dried over anhyd. $MgSO_4$. After filtration, volatile solvents were removed in vacuo. The residual oil (14.4 g) was identified as bis(3-acetylglyceryl) succinate.

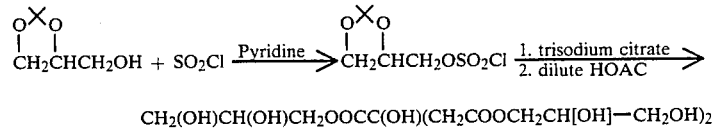

$CH_2(OH)CH(OH)CH_2OOCC(OH)(CH_2COOCH_2CH[OH]-CH_2OH)_2$

These polyesters can be acylated as above.

The invention will be more fully understood from a study of the following examples.

EXAMPLE 1

Preparation of Diglyceryl Succinate 30.4 g glycerol, 15 g succinic anhydride and 1 g p-toluenesulfonic acid hydrate were mixed with 250 ml dioxane, placed in a RB flask, stirred and heated at reflux under a Sohxlet system for 93 hours. The clear yellow reaction solution was cooled to room temperature. Once cooled it was stirred with a large excess of anhy-

EXAMPLE 5

The compounds of Examples 1, 2, 3 or 4 were dissolved in water to a concentration calculated to yield 0.5 Kcal/ml (Table 2). 200 ml of each of the solutions were prepared by sterile filtration. The sterile solutions were continuously infused into rats at a rate of 120 ml/Kg/day. The rats were able to metabolize the polyesters and to subsist on them in the absence of oral food intake.

We claim:

1. A sterile, aqueous nutrient solution for intravenous administration of an effective amount, of a compound having the formula G—[OOCACOOY]—$_n$E wherein G is hydrogen, the residue of a monosaccharide, a nontoxic, biologically available normal or branched chain aliphatic group containing at least one hydroxyl or hydroxyl and keto substitutent or the radical (QCOO)$_d$—Y— where QCOO— and Y are defined below and d is 1 or 2;

QCOO— is acetyl, acetoacetyl, butyryl or the residue of a nontoxic, biologically available normal or branched chain hydroxy or keto substituted aliphatic carboxylic acid having more than 4 carbon atoms;

Y is the residue of a monosaccharide, a nontoxic, biologically available normal or branched chain aliphatic group containing at least two hydroxyl substitutents;

n is from 1 to about 15; provided that when n>1, —OOCACOOY— may be the same or different;

E is hydroxyl, —OOCACOOH, or —(OOCQ)$_D$;

A is —(CH$_2$)a—C(R)(Z)(CH$_2$)$_b$C(R')(R")—, wherein

R is hydrogen or hydroxyl;

Z is carboxyl, —OOCACOOH, —OOCQ, hydrogen or hydroxyl; provided that were R is hydroxyl, Z is not hydroxyl, and that R and Z may be taken together to be oxy;

a is zero or an integer from 1 to about 5;

b is zero or an integer from 1 to about 5; provided that the sum of a and b is an even number or zero; and R' and R" are both hydrogen, hydrogen and hydroxy or taken together, oxy;

and physiologically acceptable salts thereof.

2. The composition of claim 1 wherein G is the residue of a monosaccharide or glycerol.

3. The composition of claim 1 wherein QCOO— is a beta keto or an alpha-hydroxy carboxylic acid residue.

4. The composition of claim 1 wherein QCOO— is a 3 or a 5 and 7 hydroxy substituted carboxylic acid residue.

5. The composition of claim 1 wherein n is greater than 1 but no more than 15 and the groups —OOCACOOY— are the same.

6. The composition of claim 1 wherein QCOO— is

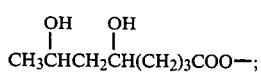
CH$_3$CHCH$_2$CH(CH$_2$)$_3$COO—;
(with OH, OH substituents)

CH$_3$CCH$_2$COO—;
(with =O)

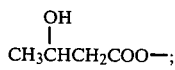
CH$_3$CHCH$_2$COO—;
(with OH)

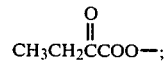
CH$_3$CH$_2$CCOO—;
(with =O)

CH$_3$CH$_2$CH(CH$_3$)CCOO—; or
(with =O)

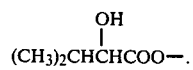
(CH$_3$)$_2$CHCHCOO—.
(with OH)

7. The composition of claim 1 wherein Y is the residue of a monosaccharide or glycerol.

8. The composition of claim 1 wherein G is (CH$_2$OH)$_2$CH—, CH$_2$(OH)CH(OH)CH$_2$—, 3-hydroxybutyrylglyceryl or acetoacetylglyceryl and Y is —CH$_2$CH(OH)CH$_2$—, —CH$_2$CH(CH$_2$OH)— or —CH$_2$CH$_2$CH(CH$_3$)—.

9. The composition of claim 1 wherein R is hydroxyl, R' is hydrogen and R" is hydroxyl.

10. The composition of claim 5 wherein a is 1 or 3 and b is 1 or 3.

11. The composition of claim 1 wherein R, R' and R" are hydrogen and a+b is 0 or 2.

12. The composition of claim 1 wherein Y is short chain branched alkylene.

13. The composition of claim 12 wherein Y is —CH$_2$CH$_2$CH(CH$_3$)—.

14. The composition of claim 1 wherein E is hydroxyl.

15. The composition of claim 1 wherein G is the residue of a monosaccharide and Y is either a short chain branched or normal alkylene, or —CH$_2$CH(OH)CH$_2$—.

16. The composition of claim 1 wherein n is about from 1 to 10.

17. The composition of claim 1 wherein G is acetoacetylglyceryl, Y is —CH$_2$CH(OH)CH$_2$—, n is 1, A is —(CH$_2$)$_2$—, and E is acetoacetyl.

18. The composition of claim 1 wherein A is —CH$_2$CH(OH)—.

19. The composition of claim 1 wherein the monosaccharide is a reducing sugar.

20. The composition of claim 19 wherein the sugar is glucose or fructose.

21. The composition of claim 1 wherein the monosaccharide is a hexose or pentose.

22. The composition of claim 1 wherein G is a sugar alcohol.

23. The composition of claim 22 wherein the sugar alcohol is mannitol or sorbitol.

24. The composition of claim 1 wherein G is the residue of glycerol or is the radical CH$_3$CH(OH)CH$_2$CH(OH)(CH$_2$)$_3$COOCH$_2$CH(OH)CH$_2$—.

25. The composition of claim 1 wherein E is QCOO—.

26. The composition of claim 1 wherein the concentration of compound in solution is about from 5 to 15 mole percent.

27. The composition of claim 1 which is essentially free of biologically active contaminants.

28. The composition of claim 26 wherein n is 1 to 3.

29. The composition of claim 1 sealed in a container having means for making fluid communication with the circulation of a patient.

30. The composition of claim 1 sterile sealed in a flexible, thermoplastic container.

31. The composition of claim 1 wherein the aqueous solution also contains amino acids suitable for nutrition.

32. The composition of claim 31 wherein the amino acids are a nutritionally balanced mixture of essential amino acids.

33. The composition of claim 1 wherein the solution also contains a monosaccharide.

34. The composition of claim 1 wherein the salt is alkali metal or amino acid.

35. The composition of claim 1 comprising mixtures of two or more of the compounds.

36. The composition of claim 1 wherein the compound is dissolved in the solution to a concentration giving an osmolarity less than about 600 mOsm.

37. The composition of claim 1 which is essentially free of water insoluble substances.

38. A method for the nutritional support of a patient receiving otherwise inadequate nutrition, comprising administering to the patient an effective amount of the composition of claim 1.

39. The method of claim 38 wherein the composition is administered by infusion into a peripheral vein.

40. The water-soluble compound

G$\{$OOC(CH$_2$)$_2$COOY$\}_n$E wherein G is (QCOO)—$_d$—Y—, with QCOO— being a radical of the formula $$\underset{\underset{CH_3}{|}}{OH} \underset{\underset{}{|}}{OH}$$
CH$_3$CHCH$_2$CH(CH$_2$)$_3$COO—;

$$\underset{\underset{}{\|}}{O}$$
CH$_3$CCH$_2$COO—;

OH
|
CH$_3$CHCH$_2$COO—;

$$\underset{\underset{}{\|}}{O}$$
CH$_3$CH$_2$CCOO—;

$$\underset{\underset{}{\|}}{O}$$
CH$_3$CH$_2$CH(CH$_3$)CCOO—; or

OH
|
(CH$_3$)$_2$CHCHCOO—

Y is —CH$_2$CH(OF)CH$_2$— or —CH$_2$CH$_2$CH(CH$_3$)—;
n is 1 or 3
E is hydroxyl or —OOCQ as defined above; and
d is 1 or 2.

41. The water-soluble compound

G$\{$(OOC(CH$_2$)$_2$COOY$\}_n$E wherein
G is CH$_2$OHCHOHCOO— or (QCOO)$_d$—Y—, with QCOO— being a radical of the formula;

$$\underset{\underset{}{\|}}{O}$$
CH$_3$CCH$_2$COO—;

OH
|
CH$_3$CHCH$_2$COO—; or $$\underset{\underset{}{\|}}{O}$$
CH$_3$CH$_2$CCOO—;

Y is —CH$_2$CH(OH)CH$_2$— or —CH$_2$CH$_2$CH(CH$_3$)—;
n is 1;
E is hydroxyl or —OOCQ as defined above; and
d is 1.

42. The nutrient composition containing an effective amount of the compound of claim 41 is aqueous solution suitable for administration to a patient.

43. A method for the nutrient support of a patient receiving otherwise inadequate nutrition, comprising administering to the patient an effective amount of the compound of claim 41.

44. The composition of claim 1 wherein the compound is thermally stable under sterilization conditions.

45. The compound of claim 40 wherein the compound is thermally stable under sterilization conditions.

46. The compound of claim 41 wherein the compound is thermally stable under sterilization conditions.

47. A nutrient composition which is an aqueous solution, suitable for intravenous administration of an effective amount, of the compound of claim 40.

48. A nutrient composition which is an aqueous solution, suitable for intravenous administration of an effective amount, of the compound of claim 41.

49. A sterile aqueous solution for intravenous administration of claim 1 in which A is the condensed residue of malic acid.

50. A sterile, aqueous solution for intravenous administration of claim 1 which contains diglyceryl succinate.

51. A sterile, aqueous solution for intravenous administration of claim 1 which includes bis(3-hydroxybutyryl) succinate.

52. A sterile aqueous solution for intravenous administration of claim 1 which includes bis(3-acetylglyceryl) succinate.

* * * * *